United States Patent [19]

Yamada et al.

[11] Patent Number: 4,615,787

[45] Date of Patent: Oct. 7, 1986

[54] AIR/FUEL RATIO DETECTOR

[75] Inventors: Tetsusyo Yamada; Shintaro Hirate, both of Aichi, Japan

[73] Assignees: Mitsubishi Denki NGK Spark Plug Co. Ltd., Aichi; Kabushiki Kaisha, Tokyo, both of Japan

[21] Appl. No.: 681,333

[22] Filed: Dec. 13, 1984

[30] Foreign Application Priority Data

Dec. 15, 1983 [JP] Japan ................................ 58-237621

[51] Int. Cl.$^4$ ............................................ G01N 27/56
[52] U.S. Cl. .................................... 204/406; 204/407; 204/424; 123/440; 60/276
[58] Field of Search ...................... 123/440, 489, 589; 60/276; 204/406, 407, 424

[56] References Cited

U.S. PATENT DOCUMENTS 4,363,306 12/1982 Sone et al. ........................... 123/440
4,499,880 2/1985 Miki et al. ........................... 123/489

FOREIGN PATENT DOCUMENTS 0057899 8/1982 European Pat. Off. .

Primary Examiner—Andrew M. Dolinar
Attorney, Agent, or Firm—Sughrue, Mion, Zinn, Macpeak & Seas

[57] ABSTRACT

An air/fuel ratio detector providing an unambiguous output for both fuel-rich and fuel-lean regions is disclosed. The detector includes a solid-electrolyte oxygen-concentration-difference-actuated electrochemical cell sensor element and a solid-electrolyte oxygen pump element, each element being in the form of an oxygen-ion-conductive solid electrolyte having a porous electrode formed on both sides thereof. The electrochemical cell sensor element is disposed to face the pump element with a small gap therebetween. An air compartment open to the atmosphere is formed on the side of the pump element opposite the small gap. One terminal of the pump element is connected to a switch having at least two positions, one providing connection to a varying current source for maintaining the electromotive source of the electrochemical cell sensor at a predetermined value, and another position providing connection to a constant current source for maintaining the pump current flowing through the pump element at a fixed predetermined level. The air/fuel ratio is detected by an output signal provided by one of the electromotive force of the sensor element and the pump current.

8 Claims, 8 Drawing Figures

AIR/FUEL RATIO DETECTOR

BACKGROUND OF THE INVENTION

The present invention relates to an A/F (Air/Fuel) ratio detector for use in the measurement or control of the concentration of oxygen in exhaust gas from a burning device such as an internal combustion engine or gas burner.

An oxygen sensor composed of an ion-conductive solid electrolyte (e.g., stabilized zirconia) coated with porous electrode layers (e.g., Pt porous layers) is capable of detecting the concentration of oxygen near a theoretical (stoichiometric) A/F ratio of exhaust gas from an internal combustion engine to thereby detect the combustion efficiency of the engine. Detection is carried out by sensing a change in an electromotive force that is produced by the difference between the partial oxygen pressure of the exhaust gas and that of atmospheric air. This type of oxygen sensor is presently used in numerous applications, for example, in an automobile for the purpose of controlling its internal combustion engine to run at the theoretical air/fuel ration.

The conventional oxygen sensor exhibits a large amount of change in its output if the operating A/F ratio (which is the weight ratio of air to fuel) is near the theoretical value of 14.7, but otherwise the resulting change in output is negligibly small. Therefore, the output from this sensor cannot be effectively used for an engine operating at an A/F ratio other than near the theoretical value.

Japanese Published Unexamined Patent Application No. 153155/1983 shows an oxygen concentration detector having a quick response. This detector is composed of a pair of oxygen-ion-conductive solid electrolyte plates each having an electrode layer on both sides in a selected area close to one end thereof. The two plates are fixed parallel to each other and spaced to provide a gap in an area corresponding to that selected area having the electrode layers. One electrolyte plate with electrode layers is used as an oxygen pump element, and the other plate also having electrode layers is used as an electrochemical cell sensor element that operates in response to the difference in oxygen concentration between the ambient atmosphere and the gap between the two plates. Although this detector has a quick response, according to experiments conducted by the present inventors, the output of the sensor is ambiguous. That is, when this device is operated in a fuel-rich region having an A/F ratio lower than the theoretical velue of 14.7, the direction of change of the output away from the theoretical value is the same as that for operation in the fuel-lean region. Because of the existence of two possible A/F ratios for a single output, the sensor can be used only when it is definitely known whether the burning device to be controlled is operating in the fuel-rich or fuel-lean region. Furthermore, the present inventors have found it difficult to detect an operating A/F ratio at or near the theoretical A/F ratio, or to provide feedback control over the A/F ratio regions.

SUMMARY OF THE INVENTION

Accordingly, an object of the present invention is to provide an A/F ratio detector that is capable of accurately and with a quick response time detecting the operating A/F ratio of a burner such as an internal combustion engine whether it is operating in the fuel-rich region, fuel-lean region or at the theoretical A/F ration, and detecting in what part of the fuel-rich and fuel-lean regions the burner is operating.

Another object of the present invention is to provide an A/F ratio detector that enables precise and simple feedback control over the A/F ration in all operating regions.

The above and other objects of the present invention are met by an A/F ratio detector comprising a solid-electrolyte oxygen-concentration-difference-actuated electrochemical cell sensor element and a solid-electrolyte oxygen pump element, each element being in the form of an oxygen-ion-conductive solid electrolyte having a porous electrode formed on both sides with the electrochemical cell sensor element being disposed to face the pump element with a small gap therebetween. An air compartment which is open to the atmosphere is formed on that side of the pump element opposite the small gap. An electric current is passed through the oxygen pump element so that oxygen is pumped into the small gap from the air compartment. The resulting output of the electrochemical cell sensor element is used to determine whether the gas being detected is in the fuel-rich or fuel-lean region, the air/fuel ratio being detected both by the result of the decision and by an output signal provided by either the electromotive force of the sensor element or the pump current flowing through the pump element. In a preferred embodiment, one end of the pump element is connected to a switch having two positions, one providing connection to a varying current source that maintains the electromotive force of the electrochemical cell sensor element at a predetermined level, and the other providing connection to a constant-current source that maintains the pump current flowing through the pump element at a predetermined level. The A/F ratio is indicated by an output signal provided by either the electromotive force of the sensor element or the pump current flowing through the pump element.

With this arrangement, the detector of the present invention has the advantage of enabling accurate and responsive detection of the A/F ratio for all or part of the operating range including both the fuel-rich, fuel-lean regions and the theoretical A/F ratio. Furthermore, the detector has a long service life as it requires only a small pump current (i.e., low current density on the electrode surface) for producing a given output signal.

DESCRIPTION OF THE PREFERRED EMBODIMENTS

Preferred embodiments of an A/F ratio detector of the present invention will hereunder be described with reference to the accompanying drawings.

Figure 1:
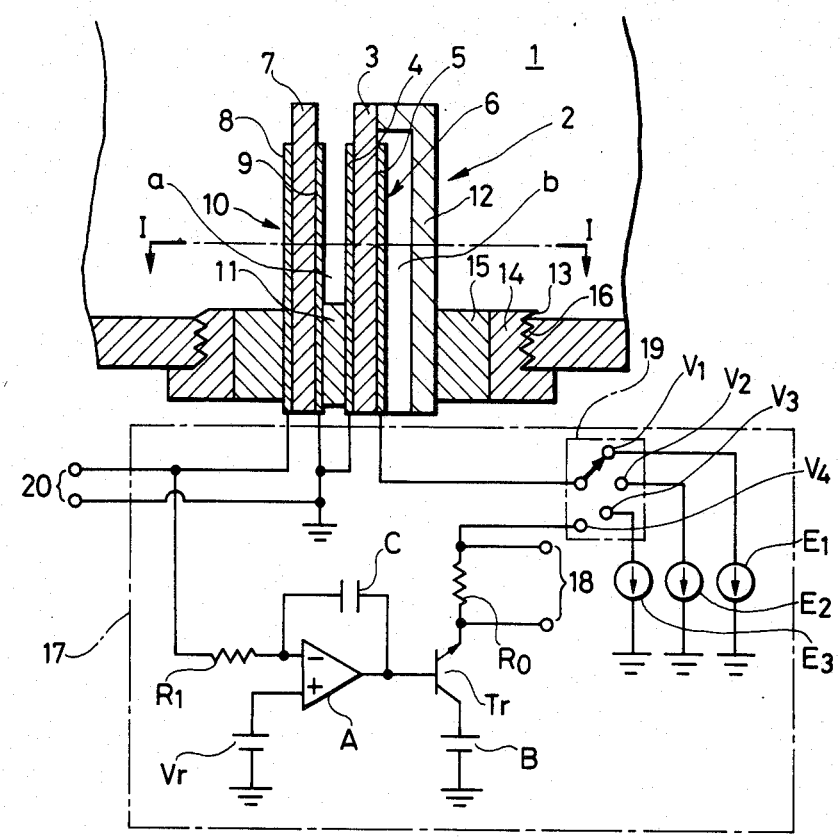
FIG. 1 shows, in cross section, an A/F ratio detector according to a first preferred embodiment of the present invention.
Figure 2:
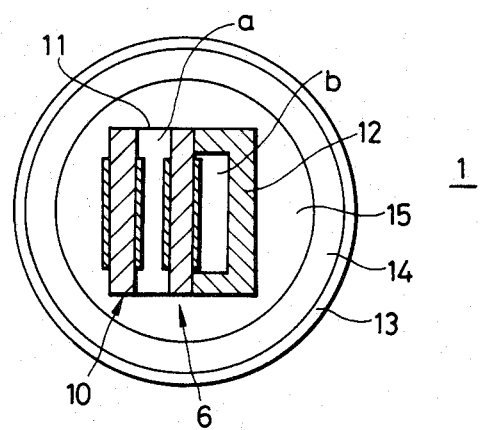
FIG. 2 is a cross section taken along a line I—I in FIG. 1.

FIGS. 1 and 2 show the detector according to a first preferred embodiment of the invention. The detector is mounted in an exhaust pipe 1 of an internal combustion engine. The probe 2 of the detector includes a solid-electrolyte oxygen pump element 6 and a solid-electrolyte oxygen-concentration-difference-actuated electrochemical cell sensor element 10. The pump element 6 consists of an oxygen ion-conductive solid-electrolyte plate 3 (about 0.5 mm thick and preferably made of stabilized zirconia) having a porous Pt electrode layer 4 formed on one side and another porous Pt electrode layer 5 formed on the other side. Each Pt layer has a thickness of about 20 μm and may be formed by a thick-film deposition technique. The electrochemical cell sensor element 10 also consists of an ion-conductive solid-electrolyte plate 7 (about 0.5 mm thick and preferably made of stabilized zirconia) having a porous platinum electrode layer 8 formed on one side and another porous Pt electrode layer 9 formed on the other side.

The pump element 6 and the sensor element 10 are mounted side by side in the exhaust pipe 1 with a gap a therebetween, typically about 0.1 mm or less in width, and are fixed together by filling the gap at the base portion with a heat-resistive and insulating spacer 11. An adhesive filler may be used as the spacer. The porous Pt electrode layer 5 of the pump element 6 formed on the side opposite the gap from the sensor element 10 is provided with a wall 12 made of a heat-resistive and impermeable material such as a metal or ceramic to form an air compartment b which is open to the atmosphere. This wall 12 is sealed around the porous Pt electrode layer 5, except for its base portion, so that this layer can communicate with the atmosphere.

A support 14 with a male thread 13 is fixed around the base portion of the combined pump element 6, sensor element 10 and wall 12 by means of a heat-resistive and insulating adhesive member 15. The probe 2 is securely mounted in the exhaust pipe 1 by engaging the male thread 13 with a female thread 16 in the exhaust pipe 1.

In the detection probe of the above embodiment of the present invention, the pump element and the sensor element are mounted side by side in the exhaust pipe with a gap therebetween and are fixed together by filling the gap at the base portions with a spacer. It is preferable to sufficiently open peripheral edges of the pump element and the sensor element to the exhaust gases so as to increase the responsivity of the probe. However, the present invention is not limited to the configuration of open edges of the pump element and the sensor element except for their base portions. For example, it is possible to provide support members between the solid-electrolyte plates of the pump element and the sensor element for more readily regulating the gap dimensions (as far as the support member does not cause any considerable reduction of responsivity).

Also, the size of the gap between the pump element and the sensor element is preferably in a range from 0.01 to 0.15 mm. If the gap is too narrow, the responsivity is reduced. The electrode layer which defines the small gap is preferably a porous thick layer having a mean porosity of about 10–40% (as determined by a porosimeter of the pressurized mercury type) in consideration of its diffusion resistance against component gases such as oxygen.

Furthermore, in the case that the electrode layer is formed by a suitable thin-film deposition technique, it is preferable to provide thereon a porous layer of a material such as a ceramic material to which may be added a catalytic agent for obtaining a catalytic action.

An example of the electronic control unit for use in association with the detector of the present invention is indicated in FIG. 1 by reference numeral 17. The EMF e generated between the porous Pt electrode layers 8 and 9 of the electrochemical cell sensor element 10 is applied to the inverting input terminal of the operating amplifier A through a resistor $R_1$, and the amplifier produces an output proportional to the difference between e and a reference voltage $V_r$ applied to the noninverting input terminal of the amplifier. The output of the amplifier drives a transistor Tr to control the pump current $I_p$ flowing between the Pt electrode layers 4 and 5 of the pump element 6 in such a manner that $I_p$ is sufficient to maintain e at the constant level $V_r$. The control unit 17 also includes a resistor $R_0$ to provide output terminals 18 with an output signal corresponding to the pump current $I_p$ supplied from a d.c. source B. The output of the amplifier A and its inverting input are connected by a capacitor C. The pump element 6 has at one end a switch 19 providing for selection between four positions $V_1$, $V_2$, $V_3$, and $V_4$. In order to cause the pump element 6 to pump oxygen into the small gap a from the air compartment b, $V_1$, $V_2$ and $V_3$ are respectively connected to three constant current sources $E_1$ (50 mA), $E_2$ (30 mA) and $E_3$ (15 mA). The other position $V_4$ is connected to one end of the resistor $R_0$ so as to obtain an output signal corresponding to the pump current $I_p$. The control unit 17 also includes an output terminal 20 for detecting the EMF generated across the sensor element 10.

Figure 3:
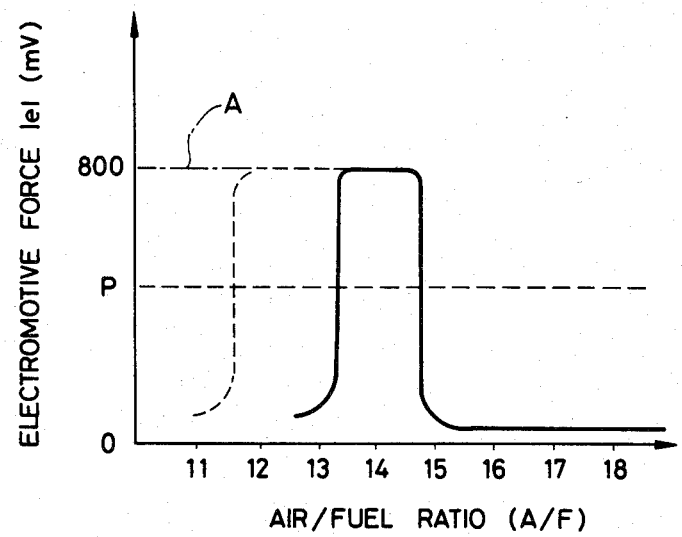
FIG. 3 is a characteristic curve showing the A/F ratio vs. the EMF e of an oxygen-concentration-difference-actuated electrochemical cell sensor element, with the pump-in current $I_p$ that flows through an oxygen pump element as a parameter ($I_p < 0$)
Figure 4:
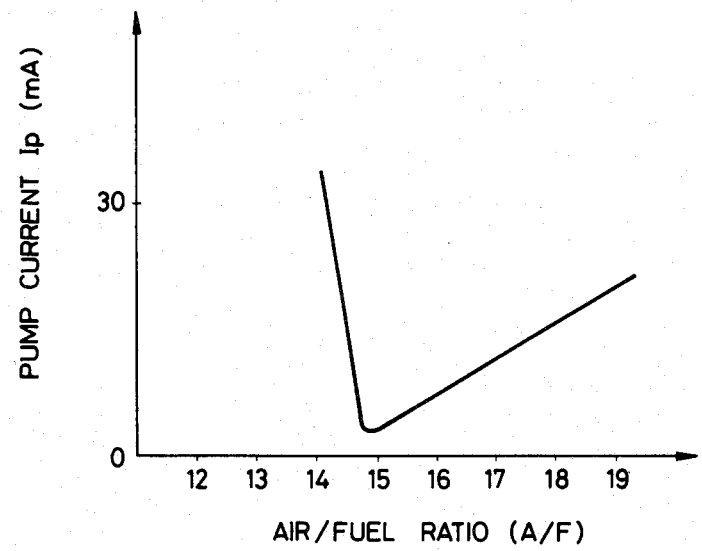
FIG. 4 is a characteristic curve showing the A/F ratio vs. pump-out current $I_p$ ($I_p > 0$) flowing through the pump element, with the EMF of the sensor element held constant ($e > 0$)

Two characteristic curves for the detector probe 2 shown in FIGS. 1 and 2 are illustrated in FIGS. 3 and 4. FIG. 3 shows the profile of A/F ratio vs. EMF (e<0) for the case where oxygen is pumped by the pump element 6 into the small gap a from the air compartment b. The parameter $I_p$ is varied at 50 mA, 30 mA and 15 mA by connecting the pump element 6 to constant-current sources $E_1$, $E_2$ and $E_3$, respectively. When $I_p$ is held at 50 mA or higher, a constant EMF e can be produced, even in the fuel-rich region where the A/F ratio is significantly smaller than the theoretical value of 14.7, as indicated by A in Fig. 3. At about the theoretical value of 14.7, e drops suddenly, and in the fuel-lean region (A/F>14.7), e is negligibly small. When $I_p$ is held at 30 mA, a constant EMF develops at an A/F ratio between 11 and 12, and at about the theoretical value of 14.7, there occurs a sudden drop in EMF. In the fuel-lean region (A/F<14.7), e is negligible. When $I_p$ is held at 15 mA, a constant EMF develops suddenly at an A/F ratio between 13 and 14, and at about the theoretical value of 14.7, there occurs a sudden drop in EMF. In the fuel-lean region (A/F>14.7), the EMF is negligible. In short, FIG. 3 illustrates the facts that the A/F ratio curve for the fuel-rich region has a knee point at which the EMF e of the sensor element 10 changes suddenly and that this knee point varies with the pump-in current flowing through the pump element 6. This characteristic may be used to perform feedback control for obtaining a desired level of A/F ratio in the fuel-rich region.

FIG. 4 shows the profile of A/F ratio vs. $I_p$ for a reference voltage $V_r$ of, for example, 100 mV. When the electromotive force e is at 100 mV, $I_p$ decreases suddenly in the fuel-rich region (A/F<14.7), and in the fuel-lean region (A/F>14.7), $I_p$ increases gradually with increasing A/F ratio.

The detector according to the embodiment shown in FIGS. 1 and 2 use the characteristics depicted in Figs. 3 and 4. By selecting the $V_1$ position of the switch 19, the characteristic indicated by line A in FIG. 3 is obtained at the EMF detecting output terminal 20. Making use of this characteristic, a reference point P is set between maximum and minimum EMPs so that the detector senses both the fuel-rich region ($V_0$>P) and the fuel-lean region ($V_0$<P). When the engine is running or is to be run in the fuel-rich region, position $V_1$ is selected for confirming that e is greater or has become greater than point P. Based on this information, position $V_1$ is switched to either $V_2$ or $V_3$ for the purpose of controlling the operating A/F ratio of the engine in the fuel-rich region. Constant current sources $E_2$ and $E_3$ to which $V_2$ and $V_3$ are connected may have various outputs which are selectable for performing a desired A/F ratio measurement or control over a wide range of the fuel-rich region. For instance, when the engine is to be operated in the fuel-lean region, the position $V_1$ may be selected. After confirming that this EMF e has become smaller than the point P, the position $V_1$ is switched to $V_4$. Then, by detecting an output signal that is indicative of the A/F ratio vs. $I_p$ profile shown in FIG. 4, a desired measurement or control of the operating A/F ratio in all fuel regions may be accomplished. If the engine is to be operated at the theoretical A/F ratio (14.7), the position $V_1$ is selected and the intended control can be achieved by causing an abrupt change in the EMF e of the electrochemical cell sensor element 10. As shown above, by properly selecting the position of the switch 19, the A/F ratio of the engine can be accurately determined whether it is operating in the fuel-rich region, fuel-lean region or at the theoretical value of 14.7.

Figure 5:
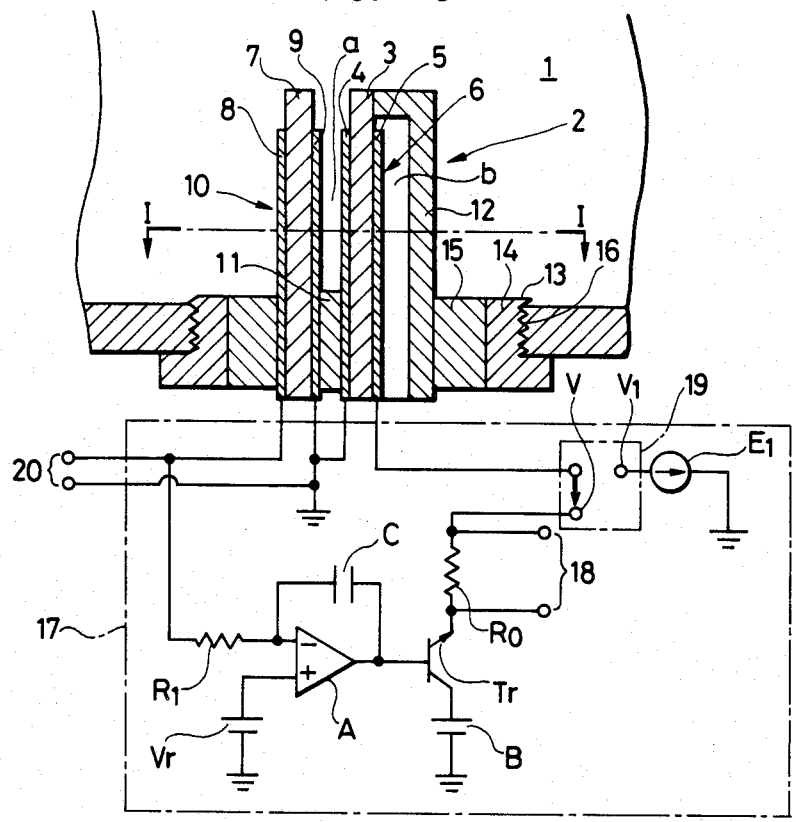
FIG. 5 shows, in cross section, an A/F ratio detector according to a second preferred embodiment of the present invention.
Figure 6:
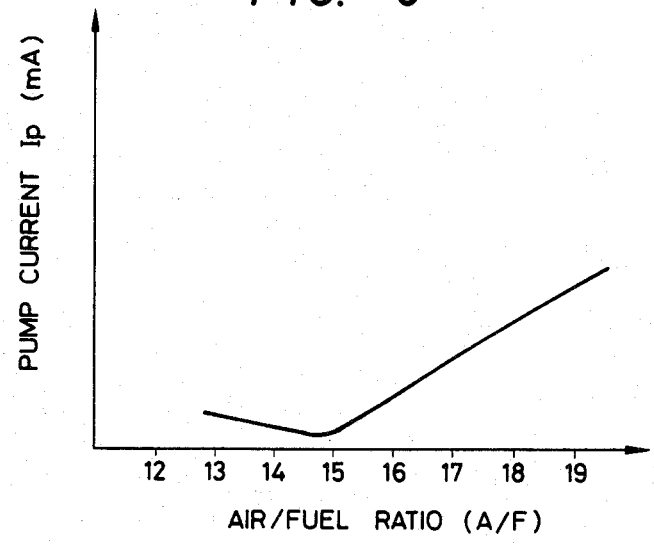
FIG. 6 is a characteristic curve showing the A/F ratio vs. pump-out current $I_p$ with the EMF of the sensor element held constant at a value which differs from the one used in FIG. 4.

If the engine is to be operated in the fuel-lean region and at the theoretical A/F ratio only, a detector having the arrangement shown in FIG. 5 may be used. This layout differs from that of FIG. 1 in that the switch 19 is connected to only one constant-current source E and has only two positions, $V_1$ and $V_4$. Needless to say, the modified detector of FIG. 5 has a characteristic which is the same as that indicated by line (A) in FIG. 3. FIG. 6 is a characteristic curve showing the A/F ratio vs. $I_p$ for the case where the reference voltage $V_r$ is held at 20 mV. As in FIG. 4, $I_p$ increases gradually in proportion to the A/F ratio in the fuel-lean region (A/F>14.7). This linearity between the A/F ratio and $I_p$ may be used in measuring or controlling the operating A/F ratio in the fuel-lean region by detecting an output signal indicative of a certain $I_p$ level flowing through the pump element 6 by selecting the position $V_4$. If the engine is to be operated at the theoretical A/F ratio (14.7), the position $V_1$ is selected to pass the current of the constant current source $E_1$ through the pump element. The intended measurement and control can be achieved accordingly.

Proportional change of $I_p$ with A/F ratio in the fuel-lean region is already known and shown in, for example, Japanese Published Unexamined Patent Application No. 153155/1983. The partial pressure of oxygen in the exhaust gas introduced into the gap a is modified by the action of the pump element 6 to a value which differs from the partial pressure of the oxygen in the exhaust gas flowing through the pipe 1. The pump current $I_p$ supplied to the pump element 6 is controlled so that the EMF e of the sensor element 10 as produced in response to the differential partial oxygen pressure is maintained constant. As a consequence of this control, the pump current $I_p$ changes in proportion to the concentration of oxygen in the exhaust gas.

The mechanism by which the EMF e of the sensor element 10 varies abruptly at an A/F ratio corresponding to a certain amount of oxygen that has been pumped by the element 6 from the air compartment b into the small gap a is as follows: The concentration of oxygen in the small gap a is determined by the balance between the amount of oxygen that is pumped into the small gap a from the air compartment b upon application of a constant current through the pump element 6 and the amount of oxygen that is consumed by or diffused into the exhaust gas through the gap a (the latter amount of oxygen varying with the A/F ratio of the exhaust gas). The difference (ratio) between the so-determined oxygen concentration in the gap a and the oxygen concentration of the exhaust gas flowing through the exhaust pipe 1 develops suddenly within a small range of A/F ratios in the fuel-rich region that corresponds to the amount of oxygen being pumped into the small gap a, and this difference causes a sudden change in the EMF e of the sensor element 10. By modifying the value of $I_p$ being supplied for causing the element 6 to pump oxygen into the small gap a from the air compartment b, the position of the knee of the A/F ratio curve at which EMF changes abruptly can be varied.

Figure 7:
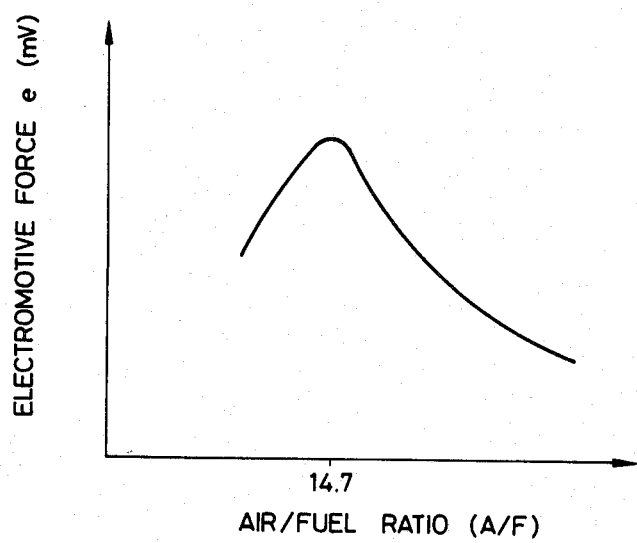
FIG. 7 is a characteristic curve showing the A/F ratio vs. the EMP e with pump-out current $I_p$ held constant.

In the embodiment shown above, the EMF e used as a signal for controlling the A/F ratio in the fuel-rich region is obtained by causing $I_p$ to flow in such a direction that oxygen is pumped into the small gap a from the air compartment b ($I_p$<0). If desired, $I_p$ may be caused to flow in the opposite direction ($I_p$>0) so that oxygen is pumped out of the gap a into the air compartment b. FIG. 7 shows the profile of A/F ratio vs. the EMF e in this modified case.

Figure 8:
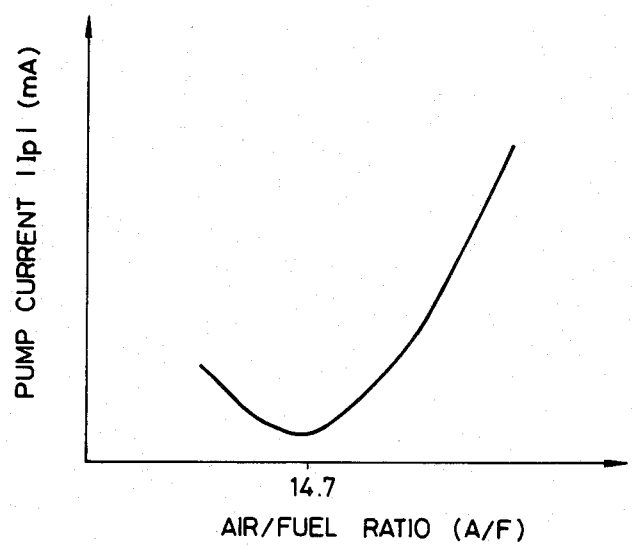
FIG. 8 is a characteristic curve showing the A/F ratio vs. pump-out current $I_p$ with the EMP of the sensor element being held constant (e<0).

Also, in the embodiments discussed above, the pump current $I_p$ used as a control signal for operation in the fuel-lean region flows in such a direction that oxygen is pumped out of the gap a into the air compartment ($I_p$>0). If desired, $I_p$ may be caused to flow in the opposite direction ($I_p$<0) so that oxygen is pumped into the gap a from the air compartment b. FIG. 8 shows the profile of $I_p$ in this modification for the case where the output of the sensor element (e<0) is held constant. The characteristic curve shown in FIG. 8 may also be used for the purposes of the present invention since the curve reflects the correlation between the operating A/F ratio and the pump current $I_p$.

The characteristics shown above that are provided by the detector of the present invention may be used either individually or in combination for the purpose of effecting feedback control over the operating A/F ratio throughout the operating range by changing the position of the switch 19 for passing a large amount of current to the pump element 6 to pump oxygen from the air compartment b to the gap a for a short period and judging whether the operating A/F ratio is in the fuel-rich or fuel-lean region from the resultant sudden change of output from the sensor element 10 near the theoretical A/F ratio.

We claim:

1. In a method for detecting the air/fuel ratio of exhaust gas with a detector comprising an electrochemical cell sensor element and an oxygen pump element, each element being in the form of an oxygen-ion-conductive solid electrolyte having a porous electrode formed on both sides thereof, said electrochemical cell sensor element being disposed to face said pump element with a small gap therebetween, exposed to the exhaust gas and an air compartment which is open to the atmosphere being formed on that side of said pump element which is opposite to said small gap, an electric current being caused to flow through said oxygen pump element so that oxygen is pumped into said small gap from the air compartment or in the opposite direction, thereby producing an electromotive force in said sensor element, said electromotive force and the current flowing through said pump element being used as a basis for detecting the air/fuel ratio of the exhaust gas, the improvement wherein a sufficient amount of current to pump oxygen from said air compartment into said small gap is caused to flow through said oxygen pump element so as to produce an abrupt change in the electromotive force of said sensor element at a stoichiometric air/fuel ratio, the electromotive force of said sensor element being used to determine whether a present air/fuel ratio is in the fuel-rich or fuel-lean region, thereby detecting the air-fuel ratio of the exhaust gas even within a small transition region including the stoichiometric ratio.

2. The method according to claim 1, wherein a sufficient amount of current to pump oxygen from said air compartment into said small gap is caused to flow through said oxygen pump element so as to produce an abrupt change in the electromotive force of said sensor element at the stoichiometric air/fuel ratio, and wherein changes in said electromotive force are applied to detect the stoichiometric air/fuel ratio.

3. In an air/fuel ratio detector comprising an electrochemical cell sensor element and a pump element, each element being in the form of an oxygen-ion-conductive solid electrolyte having a porous electrode formed on both sides thereof, said electrochemical cell sensor element being disposed to face said pump element with a small gap therebetween, exposed to exhaust gas an air compartment which is open to the atmosphere being formed on that side of said pump element which is opposite to said small gap, and a current source or current regulator for air/fuel ratio measurement being connected to said pump element so as to establish a current flow that causes oxygen to be pumped from said small gap into the air compartment or in the opposite direction, thereby producing an electromotive force in said sensor element, said electromotive force and the current flowing through said pump element being used as a basis for detecting the air/fuel ratio of the exhaust gas, the improvement wherein said detector further comprises constant current source means for providing a sufficient constant current through said pump element in such a direction that oxygen is pumped from said air compartment into the small gap, and switching means for selectively breaking the connection between said pump element and said current source means for air/fuel ratio measurement and for establishing a connection between said pump element and said constant current source means, an abrupt change in the electromotive force of said sensor element being produced at the stoichiometric air/fuel ratio by actuating said switching means for connecting said pump element to said constant current source means, said change in electromotive force being used to determine whether the present air/fuel ratio is higher or lower than the stoichiometric value, thereby detecting the air/fuel ratio of an exhaust gas even within a small transition region from the fuel-rich to fuel-lean state.

4. The air/fuel ratio detector according to claim 3, wherein said current source means for air/fuel ratio measurement comprises controllable current source means which receives the electromotive force of the oxygen pump element as a control input and which is connected to maintain said electromotive force at a predetermined level by automatic control of the current flowing through said pump element, said detector providing an air/fuel ratio signal corresponding to the current flowing through said pump element.

5. The air/fuel ratio detector according to claim 3, wherein the magnitude to the current supplied from said constant current source means is approximately 50 mA.

6. The air/fuel ratio detector according to claim 3, wherein said small gap has a width of approximately 0.01 to 0.15 mm.

7. In a method of detecting the air/fuel ratio of exhaust gas with a detector comprising an electrochemical cell sensor element and an oxygen pump element, each element being in the form of an oxygen-ion-conductive solid electrolyte having a porous electrode formed on both sides thereof, said electrochemical cell sensor element being disposed to face said pump element with a small gap therebetween, exposed to the exhaust gas and an air compartment which is open to the atmosphere being formed on that side of said pump element which is opposite to said small gap, an electric current being caused to flow through said oxygen pump element so that oxygen is pumped from said small gap into the air compartment or in the opposite direction, thereby producing an electromotive force in said sensor element, said electromotive force and the current flowing through said pump element being used as a basis for detecting the air/fuel ratio of the exhaust gas, the improvement wherein a sufficient amount of current to pump oxygen from said air compartment into said small gap is caused to flow through said pump element so as to produce an abrupt change in the electromotive force of said cell sensor element at the stoichiometric air/fuel ratio, said change in the electromotive force being used to detect the stoichiometric air/fuel ratio.

8. The method according to claim 7, wherein a signal corresponding to the magnitude of a current flowing through the oxygen pump element in such a direction that oxygen is pumped out of the small gap to enter the air compartment so as to maintain the electromotive force of the electrochemical cell sensor element at a constant level is used for detecting air/fuel ratios.

* * * * *

UNITED STATES PATENT AND TRADEMARK OFFICE
CERTIFICATE OF CORRECTION

PATENT NO. : 4,615,787

DATED : October 7, 1986

INVENTOR(S) : Tetsusyo Yamada: Shintaro Hirate

It is certified that error appears in the above-identified patent and that said Letters Patent is hereby corrected as shown below:

On the title Item [73] should read:

[73] Assignees: NGK Spark Plug Co., Ltd. Aichi, Japan and

Mitsubishi Denki Kabushiki Kaisha, Tokyo, Japan

Signed and Sealed this

Tenth Day of March, 1987

Attest:

DONALD J. QUIGG

Attesting Officer

Commissioner of Patents and Trademarks